United States Patent
Nakajima et al.

(10) Patent No.: US 8,518,412 B2
(45) Date of Patent: Aug. 27, 2013

(54) PARTIAL PEPTIDE OF LACRITIN

(75) Inventors: Takeshi Nakajima, Hyogo (JP);
Tomoko Nakajima, Hyogo (JP);
Mitsuyoshi Azuma, Hyogo (JP)

(73) Assignee: Senju Pharmaceutical Co, Ltd., Osaka-shi (JP)

( * ) Notice: Subject to any disclaimer, the term of this patent is extended or adjusted under 35 U.S.C. 154(b) by 0 days.

(21) Appl. No.: 13/496,437

(22) PCT Filed: Sep. 16, 2010

(86) PCT No.: PCT/JP2010/066611
§ 371 (c)(1),
(2), (4) Date: Apr. 10, 2012

(87) PCT Pub. No.: WO2011/034207
PCT Pub. Date: Mar. 24, 2011

(65) Prior Publication Data
US 2012/0245102 A1    Sep. 27, 2012

(30) Foreign Application Priority Data

Sep. 16, 2009  (JP) ................................ 2009-215030

(51) Int. Cl.
*A61K 38/18*  (2006.01)
*C07K 14/435* (2006.01)
*C07K 14/475* (2006.01)

(52) U.S. Cl.
USPC ....... 424/198.1; 514/1.1; 514/20.8; 514/21.2; 514/21.3; 530/300; 530/350

(58) Field of Classification Search
None
See application file for complete search history.

(56) References Cited

U.S. PATENT DOCUMENTS

| | | | |
|---|---|---|---|
| 7,320,870 B2 * | 1/2008 | Laurie et al. ................... | 435/7.1 |
| 7,459,440 B2 * | 12/2008 | Laurie et al. ................... | 514/1.1 |
| 7,648,964 B2 * | 1/2010 | Laurie et al. ................... | 514/1.1 |
| 8,383,130 B2 * | 2/2013 | Nakajima et al. .......... | 424/198.1 |
| 2003/0175285 A1 | 9/2003 | Klinguer-Hamour et al. | |
| 2011/0008891 A1 | 1/2011 | Nakajima et al. | |

FOREIGN PATENT DOCUMENTS

| | | |
|---|---|---|
| JP | 2003-528112 A | 9/2003 |
| WO | WO 02/065943 A2 | 8/2002 |
| WO | WO 2005/119899 A2 | 12/2005 |
| WO | WO 2008/033477 A2 | 3/2008 |
| WO | WO 2009/116639 A1 | 9/2009 |

OTHER PUBLICATIONS

English translation of WO2009/116639 (Sep. 24, 2009); 16 total pages.*
"Superficial punctate keratitis", downloaded from merckmanuals.com/home/eye_disorders/corneal_disorders/superficial_punctate_keratitis.html on Nov. 2, 2012; 2 pages.*
"Corneal Ulcer", downloaded from merckmanuals.com/home/eye_disorders/corneal_disorders/corneal_ulcer.html on Nov. 2, 2012; 2 pages.*
Samudre et al. Lacritin, a novel human tear glycoprotein, promotes sustained basal tearing and is well tolerated. Invest Opthalamol & Vis Sci 52(9): 6265-6270, 2011.*
Samudre et al. Lacritin, a novel tear glycoprotein, stimulates tear production in rabbits without ocular toxicity. FASEB J 22: 1137, 2008.*
Sharma et al. Tumor necrosis factor-induced apoptosis in corneal epithelial cells is attenuated by novel lacrimal glycoprotein, lacritin. IOVS 46 (Suppl S): 2119, 2005.*
McKown et al. Lacritin and other new proteins of the lacrimal functional unit. Exp Eye Res 88: 848-858, 2009.*
"Cells and Tissues" in Cell Biology: A Short Course, Second Edition. Stephen Bolsover et al. New Jersey: John Wiley & Sons, Inc., 2004, pp. 1-18.*
Frisch et al., *The Journal of Cell Biology*, 124(4): 619-626 (1994).
Ma et al., *The Journal of Cell Biology*, 174(7): 1097-1106 (2006).
Sanghi et al., *J. Mol. Biol.*, 310: 127-139 (2001).
Wang et al., *The Journal of Cell Biology*, 174(5): 689-700 (2006).
Japanese Patent Office, International Search Report in International Patent Application No. PCT/JP2010/066611 (Dec. 28, 2010).
Li et al., *Journal of Proteome Research*, 4: 2052-2061 (2005).
European Patent Office, Extended European Search Report in European Patent Application No. 10817319.6 (Dec. 5, 2012).

* cited by examiner

*Primary Examiner* — Bridget E Bunner
(74) *Attorney, Agent, or Firm* — Leydig, Voit & Mayer, Ltd.

(57) ABSTRACT

The invention provides a polypeptide containing an amino acid sequence, which is a particular partial sequence of lacritin and is characterized by gyro-modification of N-terminal glutamine. The polypeptide promotes adhesion between a cell and extracellular matrix and is stable in aqueous solution.

5 Claims, 3 Drawing Sheets

FIG.1

Influence of pyro-modification on stability of partial peptide of lacritin

Lac50-83

| preservation condition | Initial residual rate (%) | 7 days-preservation residual rate (%) | 14 days-preservation residual rate (%) | 21 days-preservation residual rate (%) | 28 days-preservation residual rate (%) |
|---|---|---|---|---|---|
| 4°C | 100.0 | 95.5* | 92.7 | 89.6 | 85.8 |
| 25°C | 100.0 | 62.1* | 41.7 | 30.2 | 23.5 |
| 40°C | 100.0 | 23.9* | 16.3 | 16.4 | 15.4 |
| 60°C | 100.0 | 19.8* | 18.6 | 20.0 | 16.9 |

(residual rate: *; water correction (-), others; water correction (+))

Pyr Lac50-83

| preservation condition | Initial residual rate (%) | 7 days-preservation residual rate (%) | 14 days-preservation residual rate (%) | 21 days-preservation residual rate (%) | 28 days-preservation residual rate (%) |
|---|---|---|---|---|---|
| 4°C | 100.0 | 99.4 | 100.0 | 99.3 | 100.1 |
| 25°C | 100.0 | 98.6 | 98.9 | 99.3 | 99.9 |
| 40°C | 100.0 | 97.9 | 97.5 | 93.5 | 96.4 |
| 60°C | 100.0 | 89.4 | 81.0 | 66.6 | 58.2 |

(residual rate: water correction (+))

Mean±S.D. (n=4)
**; P<0.01 (Dunnett's test, vs. PBS)

PARTIAL PEPTIDE OF LACRITIN

TECHNICAL FIELD

The present invention relates to a polypeptide having a particular partial sequence of lacritin which is a protein in the tear fluid. Specifically, the present invention relates to a modified partial peptide of lacritin.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,714 bytes ASCII (Text) file named "710015ReplacementSequenceListing-2nd.txt," created May 22, 2012.

BACKGROUND ART

It is known that cell-extracellular matrix adhesion is involved in various functions such as cell survival, motility and the like. This is a process essential for controlling the normal development of individual, maintenance of tissues, or recovery from damage or infection. An abnormality in the signaling pathway based on such cell adhesion sometimes leads to abnormal development, circulatory diseases or transformation or metastasis of the cells.

In addition, it has been reported that when the cell-extracellular matrix adhesion is inhibited, the cells reach cell death called "anoikis", and therefore, adhesion to an extracellular matrix is important for the survival of the cells (see non-patent document 1).

Lacritin is a protein identified as a tear secretion promoting factor or a growth-factor-like protein (see patent documents 1 and 2 and non-patent document 2). For lacritin, the following 1) to 5) are reported:
1) Lacritin has an activity as a growth factor for a corneal epithelial cell and a lacrimal gland acinar cell.
2) Lacritin shows a promoting effect on tear protein secretion.
3) Lacritin is expressed in a cell derived from tissues such as the lacrimal gland, parotid gland, minor salivary gland, submandibular gland, thyroid gland, mammary gland and corneal epithelium.
4) Eye drops containing lacritin are likely to be useful in the treatment of ocular diseases such as dry eye syndrome, Sjogren's syndrome, and corneal epithelial wounds.
5) Compounds that bind to lacritin or lacritin receptors can be screened for using a cell expressing a lacritin receptor with a lacritin-dependent calcium signal as an index.

In addition, it has been reported that lacritin or a peptide thereof partly defective in the both terminals has an action to promote division of salivary gland cells in a detection test of $^3$H-thymidine uptake (see non-patent document 3).

However, it has not been reported that lacritin or a fragment thereof (partial peptide) is involved in adhesion between a cell and extracellular matrix adhesion.

On the other hand, it is known that polypeptide generally having glutamine or glutamic acid on the N-terminal is sometimes unstable in an aqueous solution. As a stabilization method, pyro-modification and the like, namely, a method including synthesis of pyroglutamic acid derivative and the like, are known. However, pyro-modification and the like has been reported to impair inherent activity (patent document 3).
patent document 1: WO02/065943
patent document 2: WO05/119899
patent document 3: JP-A-2003-528112
non-patent document 1: Frisch, S. M. et al., Journal of Cell Biology 124, pp. 619-626 (1994)
non-patent document 2: Sanghi, S. et al., Journal of Molecular Biology 310, pp. 127-139 (2001)
non-patent document 3: Wang, J. et al. Journal of Cell Biology 174, pp. 689-700 (2006)

SUMMARY OF INVENTION

Technical Problem

An object of the present invention is to provide a substance capable of promoting adhesion between a cell and an extracellular matrix, particularly a corneal epithelial cell and an extracellular matrix, and superior in the stability in aqueous solutions.

Solution to Problem

The present inventors have conducted intensive studies in view of the above-mentioned problems, and found that a polypeptide having a particular partial sequence of lacritin can promote adhesion between a corneal epithelial cell and an extracellular matrix, and can further promote secretion of a tear protein from lacrimal gland acinar cells. Furthermore, the present inventors have succeeded in markedly improving the stability of the polypeptide in aqueous solutions while maintaining a cell adhesion promoting effect by modifying (e.g., pyro-modification) glutamine on the N-terminal of the polypeptide, which resulted in the completion of the present invention.

Accordingly, the present invention is as follows.
[1] A polypeptide comprising the amino acid sequence of SEQ ID NO: 1.
[2] An agent for promoting cell adhesion, comprising the polypeptide of the above-mentioned [1].
[3] A method of promoting cell adhesion, comprising contacting an effective concentration of the polypeptide of the above-mentioned [1] with a cell.
[4] A medicament comprising the polypeptide of the above-mentioned [1] as an effective ingredient.
[5] The medicament of the above-mentioned [4], which is aqueous liquid.
[6] The medicament of the above-mentioned [4], which is used for the prophylaxis or treatment of corneal epithelium disorder.
[7] A method for the prophylaxis or treatment of corneal epithelium disorder in a patient in need thereof, which comprises administering an effective amount of the polypeptide of the above-mentioned [1].
[8] A polypeptide comprising the amino acid sequence of SEQ ID NO: 1 for promoting cell adhesion.
[9] A polypeptide comprising the amino acid sequence of SEQ ID NO: 1 for the prophylaxis or treatment of corneal epithelium disorder.

While a preferable embodiment of the present invention is shown in the following, it should be appreciated that those of ordinary skill in the art can appropriately practice the embodiment and the like of the present invention from the explanation thereof and attached drawings, as well as conventional technique well known in the art, and readily understand the action and effect afforded by the present invention.

Advantageous Effects of Invention

The present invention can provide a novel polypeptide stable in aqueous solutions, which is capable of promoting adhesion between a cell and an extracellular matrix, particularly a corneal epithelial cell and an extracellular matrix. With such novel polypeptide, a medicament superior in preservation stability, particularly such medicament in the form of an aqueous liquid, can be provided.

A corneal epithelial sheet, which functions stably for a long time by preventing cell dropout, can be prepared by adding the polypeptide of the present invention into a culture medium for preparation of a corneal epithelial sheet for transplantation. Furthermore, the present invention can provide a medicament useful for the prophylaxis or treatment of corneal epithelium disorder.

BRIEF DESCRIPTION OF DRAWINGS

FIG. 1 shows an influence of pyro-modification on the stability of partial peptide of lacritin in aqueous solution.

DESCRIPTION OF EMBODIMENTS

Figure 2:
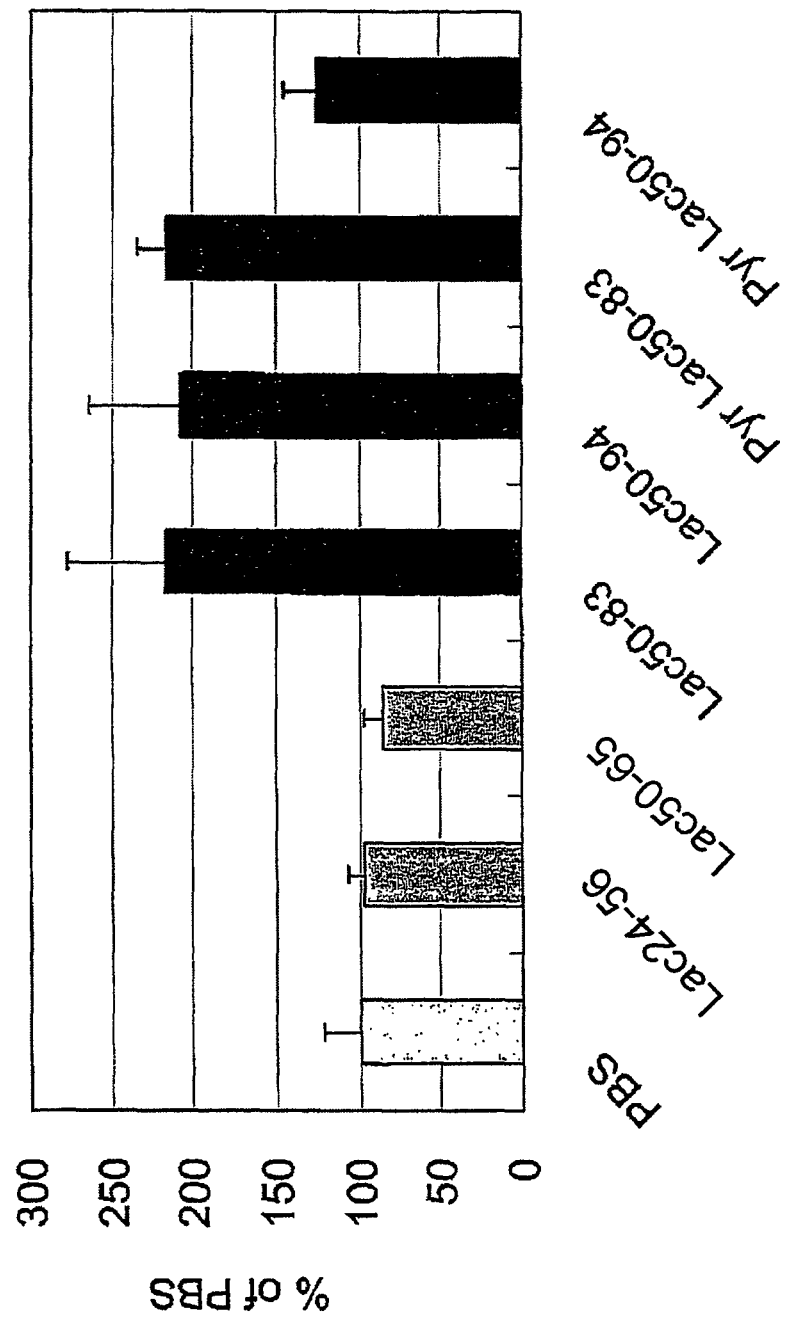
FIG. 2 is a graph showing the results of cell adhesion promoting effect of various partial peptides of lacritin, wherein the vertical axis shows the cell adhesion rate against that without addition of polypeptide as 100%, and the horizontal axis shows the kind of peptide.

The present invention is explained below. Unless particularly specified, the terms in the present specification are generally used to mean the same as in the pertinent field.

The polypeptide of the present invention is a polypeptide comprising the amino acid sequence shown by the following SEQ ID NO: 1.
Pyr Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala
(SEQ ID NO: 1)
wherein "Pyr" means pyroglutamic acid.

The amino acid sequence of SEQ ID NO: 1 corresponds to the 69th-102nd of human-derived full-length lacritin (see GenBank/EBI data bank accession Nos. NM_033277 and ay005150 (genomic); AAG32949 (extracellular glycoprotein lacritin precursor)) of SEQ ID NO: 5 consisting of 138 residues, wherein the N-terminal (i.e., 69th) glutamine is pyro-modified.

In the present invention, moreover, polypeptide having amino acid sequence shown by SEQ ID NO: 1 may contain acetylglutamine instead of N-terminal pyroglutamic acid (SEQ ID NO: 6). That is, a polypeptide wherein the N-terminal (i.e., 69th) glutamine in the 69th-102nd region of the human-derived full-length lacritin (see GenBank/EBI data bank accession Nos. NM_033277 and ay005150 (genomic); AAG32949 (extracellular glycoprotein lacritin precursor)) consisting of 138 residues, which is shown by SEQ ID NO: 5, is acetylated is also provided by the present invention.
Ac-Gln Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala (SEQ ID NO: 6)
wherein "Ac-Gln" means acetylglutamine.

Therefore, in the present specification, polypeptide wherein the N-terminal glutamine is modified by pyro-modification or acetylation is also referred to as "partial peptide of lacritin of the present invention".

Moreover, the partial peptide of lacritin of the present invention may be a polypeptide containing an amino acid sequence wherein 1-3, preferably 1-2, more preferably 1, amino acid in the amino acid sequence shown by SEQ ID NO: 1 and/or 6 may be deleted, substituted or added, as long as an activity equivalent to that of polypeptide having the aforementioned amino acid sequence shown by SEQ ID NO: 1 and/or polypeptide having the amino acid sequence shown by the aforementioned SEQ ID NO: 6, namely, the cell adhesion promoting action of the polypeptide and stability in aqueous solution, is maintained. However, the above-mentioned deletion, substitution or addition of the amino acid is applied to the amino acid other than the N-terminal, since the present invention is characterized by the modification (e.g., pyro-modification, acetylation) of the N-terminal glutamine.

In the present specification, the "amino acid" generally means "natural amino acid". However, it may be "non-natural amino acid" as long as it satisfies the object of the present invention. Here, the "natural amino acid" means an L-isomer of natural amino acid. The natural amino acid includes glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine and lysine. Unless otherwise specified, all amino acids in the present specification are L-forms. However, an embodiment using amino acid in a D-form is also within the scope of the present invention. Here, the "non-natural amino acid" means amino acid generally absent in a protein. Examples of the non-natural amino acid include D-form of norleucine, para-nitrophenylalanine, homophenylalanine, para-fluorophenylalanine, 3-amino-2-benzylpropionic acid or homoarginine and D-phenylalanine, or other modified amino acid.

In the present specification, the "deletion of amino acid" means removal of constituent amino acid from any position of the amino acid sequence.

In the present specification, the "substitution of amino acid" means substitution of the constituent amino acid with other amino acid at any position of the amino acid sequence. As the substitution of the amino acid, conservative substitution is preferable. The conservative substitution means a substitution such that amino acid is substituted by other amino acid having similar property, due to which those of ordinary skill in the art in the peptide chemistry expect the secondary structure and hydropathy property of polypeptide do not change substantially. As groups of amino acids in conservative substitution with each other, the following are generally known: (1) glycine, asparagine, glutamine, cysteine, serine, threonine and tyrosine; (2) alanine, valine, leucine, isoleucine, proline, phenylalanine, methionine and tryptophan; (3) glycine, alanine, serine, threonine and methionine; (4) leucine, isoleucine and valine; (5) glutamine and asparagine; (6) glutamic acid and aspartic acid; (7) arginine, lysine and histidine; (8) phenylalanine, tryptophan and tyrosine.

The substitution of the amino acid may be that to modified amino acid. As the modified amino acid, amino acid that underwent addition of amino-protecting group (e.g., acetylation, formylation, butyloxycarbonylation (Boc-modification), fluorenylmethoxycarbonylation (Fmoc-modification)), esterification of carboxyl group (ethylation and the like) and the like can be mentioned.

In the present specification, the "addition of amino acid" means addition of any amino acid to any position of an amino acid sequence, and includes insertion of an amino acid.

In the present specification, the "peptide" is a generic term of a substance having a peptide bond formed by dehydration of two or more of the above-mentioned amino acids (natural, non-natural amino acids) between amino group and carboxyl group. When the number of the bonded amino acids is 2, it is dipeptide, when the number is 3, it is tripeptide, when several to about dozen amino acids are bonded, it is oligopeptide, and a more number of amino acids are bonded, it is polypeptide.

In the present specification, the "partial peptide of lacritin" means a polypeptide consisting of a part of the amino acid sequence of lacritin shown by SEQ ID NO: 5.

As mentioned above, the polypeptide of the present invention may have an amino acid sequence wherein 1-3, preferably 1-2, more preferably 1, amino acid may be deleted, substituted or added, as long as it has an activity equivalent to that of polypeptide having the aforementioned amino acid sequence shown by SEQ ID NO: 1 and/or polypeptide having the amino acid sequence shown by the aforementioned SEQ ID NO: 6, and such polypeptide is also within the present invention. Here, "having an activity equivalent" means the presence of not less than about 80%, preferably not less than about 90%, of a cell adhesion promoting action of the polypeptide before deletion, substitution or addition of the amino acid, as well as the presence of not less than about 80%, preferably not less than about 90%, of the stability of the polypeptide before deletion, substitution or addition of the amino acid in aqueous solution. In the present specification, the "cell adhesion promoting action" is an action to promote adhesion between a cell and extracellular matrix (cell-substrate adhesion) or adhesion between cells, preferably an action to promote adhesion between a cell and extracellular matrix. Here, for example, when promoting cell-substrate adhesion, to "promote cell adhesion" corresponds to increasing the number of cells that have adhered to the substrate by the presence of a test polypeptide as compared to the absence thereof. Specifically, this action can be assayed as described in the below-mentioned Examples by adding a test polypeptide onto a plate coated with a suitable extracellular matrix, forming a layer of corneal epithelial cells thereon, incubating the cells for a given time, and counting the adhered cells. As the stability in aqueous solution, stability in an aqueous solution such as phosphate buffered saline (PBS) and the like can be exemplified. This action can be evaluated by adding test polypeptide to a suitable aqueous solution such as PBS and the like and, after preservation under given conditions, measuring the residual ratio of polypeptide by HPLC and the like, as described in the below-mentioned Examples.

As the superior stability of the partial peptide of lacritin of the present invention in aqueous solution, specifically, possible preservation for at least 4 weeks at 4° C.-40° C., or possible preservation for at least 2 weeks at 60° C. can be mentioned.

The polypeptide of the present invention may be in the form of a salt according to a known method. As the salt of the polypeptide, a pharmacologically acceptable salt with a base (e.g., alkali metal) or a salt with an acid, and a pharmacologically acceptable acid addition salt is particularly preferable. Examples of the pharmacologically acceptable acid addition salt include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide of the present invention can be produced by a conventional chemical synthesis method, a recombination DNA technique or the like.

When the polypeptide of the present invention is produced by a chemical synthesis method, it can be produced according to a known peptide synthesis method. Examples of the peptide synthesis method include solid phase synthesis process, liquid phase synthesis process and the like, with preference given to solid phase synthesis process. Example of the solid phase synthesis process includes Fmoc method. The Fmoc method is a method of protecting an α-amino group with a 9-fluorenylmethoxycarbonyl (Fmoc) group, and protecting a side chain functional group with a t-butyl alcohol protecting group, wherein an Fmoc-amino acid is condensed while deprotecting an Fmoc group with piperidine, which is a secondary amine, and the side chain protecting group is finally removed by weak acid such as trifluoroacetic acid. That is, a series of operations of selective removal of α-amino-protecting group and condensation of the protected amino acid is repeated from the C-terminal side of the peptide to be synthesized to construct a protected peptide chain, and the protecting group of the side chain functional group is removed to give the object peptide.

In the solid phase peptide synthesis method, synthesis by an automatic peptide synthesis apparatus is also generally used (e.g., "Shin-Seikagaku Jikken-Koza vol. 1, protein IV" (1992) edited by the Japan Biochemical Learned Society, Tokyo Kagaku Dojin; "The Peptides: Analysis, Synthesis, Biology" Vol. 1-5, ed. by E. Gross, J. Meienhofer; Vol. 6-9, ed. by S. Udenfriend, J. Meienhofer, Academic Press, New York (1979-1987)).

When the polypeptide of the present invention is produced by a recombinant DNA technique, for example, a partial peptide of lacritin wherein N-terminal is glutamine is prepared by a recombinant DNA technique and then the N-terminal glutamine is pyro-modified to obtain the polypeptide of the present invention. Firstly, primers are designed based on the base sequence of cDNA encoding the partial peptide of lacritin wherein N-terminal is glutamin and, using a suitable cDNA library as a template, the object sequence is amplified by polymerase chain reaction (PCR), whereby a cDNA encoding the polypeptide can be produced. Such PCR method is well known in the pertinent technical field and described, for example, in "PCR Protocols, A Guide to Methods and Applications", Academic Press, Michael, et al., eds., 1990. Then, a DNA encoding the polypeptide is incorporated into a suitable expression vector, which is then introduced into either eucaryote or prokaryote, and each chain is expressed to give the desired polypeptide. Examples of the host cell usable for expression of the polypeptide include, but are not limited to, prokaryote hosts such as *Escherichia coli, Bacillus subtilis* and the like, and eucaryote hosts such as yeast, fungi, insect cell, mammalian cell and the like. Vector is a single strand or double stranded nucleic acid molecule that can be transfected into a cell and is replicatable in the cell genome or independently of the cell genome. An expression vector contains a promoter region that drives DNA expression, and may further contain a transcription and translation regulating sequence, for example, TATA box, capping sequence; CAAT sequence, 3' non-coding region, enhancer and the like. Examples of the promoter to be used in a prokaryote host include bla promoter, cat promoter and lacZ promoter, and that to be used in an eucaryote host include promoter of mouse metallothionein I gene sequence, herpes virus TK promoter, SV40 early promoter, yeast glycolytic enzyme gene sequence promoter and the like. Examples of the vector include, but are not limited to, pBR322, pUC118, pUC119, λgt10, λgt11, pMAM-neo, pKRC, BPV, vaccinia, SV40, 2-micron and the like.

Expression vector preferably contains one or more markers so that a host cell containing the vector can be selected. As a marker, those affording nutrition to a complementing auxotrophic host, antibiotic resistance (e.g., ampicillin, tetracycline, neomycin, hygromycin, geneticin etc.) or heavy metal resistance (e.g., copper) can be used.

Furthermore, a vector can be constructed such that the polypeptide is secreted and expressed using a signal sequence or the polypeptide of the present invention is expressed in the form of a fusion polypeptide with different polypeptide. Using a fusion polypeptide, the stability of the polypeptide can be improved or purification can be facilitated. Construction of such an expression vector is well known in the pertinent technical field.

A vector constructed to express the polypeptide can be introduced into a suitable host cell by transformation, transfection, conjugation, protoplast fusion, electroporation, particle gun technique, calcium phosphate precipitation, direct microinjection and the like. The polypeptide can be obtained by growing a cell containing the vector in a suitable medium to produce the polypeptide, recovering a desired recombinant polypeptide from the cell or medium, and purifying the polypeptide.

A polypeptide having a modified glutamine present in the N-terminal may be synthesized using modified glutamine as a starting material by chemical synthesis and the like, and also may be synthesized by modification of glutamine present in the N-terminal of the polypeptide without N-terminal modification, which is produced as mentioned above. For example, for pyro-modification of glutamine present in the N-terminal, cyclization by intramolecular condensation of amino group of glutamine and free γ-carboxylic acid functional group it has may be performed. Examples of the method for pyro-modification include a method comprising heating polypeptide, a method comprising use of enzyme, a method comprising changing the composition of buffer, a method comprising adding salt and the like (Biotechnology and Bioengineering, Vol. 97, No. 3, Jun. 15, 2007). For acetylation of glutamine present in the N-terminal, a method comprising use of acetic anhydride and the like can be used (Molecular Immunology 40 (2003) 943-948; J. Peptide Res. 2001, 57, 528-538).

A partial peptide of lacritin that underwent pyro-modification by any method may be used in the present invention. Similarly, a partial peptide of lacritin that underwent acetylation by any method may be used in the present invention.

The polypeptide of the present invention also includes an amino acid sequence shown by SEQ ID NO: 1 and/or SEQ ID NO: 6, wherein 1-3, preferably 1-2, more preferably 1, amino acid may be deleted, substituted or added, and maintaining an activity equivalent to that of polypeptide having the aforementioned amino acid sequence shown by SEQ ID NO: 1 and/or SEQ ID NO: 6, namely, the cell adhesion promoting action of the polypeptide and stability in aqueous solution. Said polypeptide can also be produced by obtaining a cDNA encoding the polypeptide by entering the corresponding modifications into the amino acid positions deleted, substituted or added by a known means such as Kunkel method, Gapped duplex method and the like or a method analogous thereto, and subjecting the gene to a recombinant DNA technique similar to those mentioned above. A mutation can be introduced into the gene by, for example, using a mutation introduction kit based on a site-specific mutation induction method (e.g., Mutant-K (Takara Bio Inc.), Mutant-G (Takara Bio Inc.)) and the like or LA PCR in vitro Mutagenesis series kit of Takara Bio Inc.

The polypeptide of the present invention obtained as mentioned above can be isolated and purified by a known method. Examples of known isolation and purification methods include salting out, solvent precipitation, dialysis, ultrafiltration, gel filtration, SDS-polyacrylamide gel electrophoresis, ion exchange chromatography, affinity-chromatography, reversed-phase high performance liquid chromatography, isoelectric focusing and the like.

Each peptide used may be commercially available, or specifically, synthesized by contractors (e.g., Bachem, Biologica Co., Biosynthesis Inc. etc.).

The thus-obtained polypeptide of the present invention promotes adhesion between a cell and an extracellular matrix, particularly a corneal epithelial cell and an extracellular matrix. The following explains its specific use.

(1) Culture Medium Containing the Polypeptide of the Present Invention for Preparation of Corneal Epithelial Sheet The polypeptide of the present invention can particularly promote adhesion between a corneal epithelial cell and a base material during preparation of a corneal epithelial sheet for transplantation, due to the promoting effect on the adhesion between a corneal epithelial cell and an extracellular matrix.

The corneal epithelial sheet is a substitute for living cornea and used for the treatment of cornea opacity to recover visual acuity and the like. It is used for the treatment of a refractory cornea epithelial disease such as stevens-johnson syndrome, chemical trauma and the like. A corneal epithelial sheet is prepared by, for example, adding a cell such as a corneal epithelial cell and the like on a base material such as amniotic membrane, collagen sheet and the like in a serum-containing medium, culturing the cell, and layering by coculture with 3T3 fibroblast, air-lifting and the like (Ophthalmology, vol. 42, No. 3, pages 245-250, 2000). As a method for preparation of a corneal epithelial sheet, known methods described in WO03/043542, JP-A-2004-298447, JP-A-2004-261533, JP-A-2002-331025 and the like are applied.

In the production method of the corneal epithelial sheet, a known base material used for the production of a corneal epithelial sheet can be used, and any of a base material derived from a living organism and an artificially prepared base material can be used. Specifically, as a base material derived from a living organism, amniotic membrane can be mentioned, and as an artificial base material, a collagen sheet can be mentioned. The amniotic membrane covers the uterus and the outermost layer of the placenta, and is discharged from the body with the placenta during childbirth.

As a culture medium to be used for the cell culture, known culture media used for the production of a corneal epithelial sheet, such as EpiLife medium (manufactured by Cascade Biologics Inc.), DMEM/F12 medium (manufactured by Invitrogen Corporation), DMEM medium (manufactured by Invitrogen Corporation) and the like can be used, and the culture medium can contain a known serum. While the culture temperature is not particularly limited as long as the above-mentioned cells can grow well, it is generally about 15° C.-45° C. While the culture time is not particularly limited as long as the above-mentioned cell can grow well, it is generally about 1-30 days.

The polypeptide of the present invention added to a culture medium for the preparation of the corneal epithelial sheet can be an active ingredient for promoting adhesion between a corneal epithelial cell and a base material. The concentration of polypeptide in a culture medium is generally 0.0001 w/v %-0.1 w/v %, preferably 0.001 w/v %-0.01 w/v %. The polypeptide of the present invention promotes fixation between an extracellular matrix of the base material and a corneal epithelial cell, and enables preparation of a robust corneal epithelial sheet, which functions stably for a long time by preventing cell dropout.

(2) Medicament Containing Polypeptide of the Present Invention

The polypeptide of the present invention is useful as an agent for promoting cell adhesion, since it has an action to promote cell adhesion, particularly adhesion between a cell and extracellular matrix. In the present specification, the "an agent for promoting cell adhesion" means a substance having the above-mentioned "cell adhesion promoting action", particularly a substance that promotes adhesion between a cell and extracellular matrix. Here, the level of promotion of cell adhesion when, for example, it is an agent to promote adhesion between a cell and extracellular matrix, is such that addition of polypeptide of the present invention increases the number of cells that significantly adhere to the substrate. The agent for promoting adhesion of the present invention is used for a cell (e.g., corneal epithelial cell, corneal endothelium cell, conjunctival cell and the like) derived from a mammal (e.g., rat, mouse, guinea pig, bird, sheep, horse, bovine, swine, monkey, chimpanzee, human etc.), preferably a corneal epithelial cell derived from human. The extracellular matrix is not particularly limited as long as it can adhere to a cell and includes (1) fibrous protein such as collagen, elastin and the like, (2) cell adhesion glycoprotein such as fibronectin, laminin, vitronectin and the like, (3) glycoconjugate such as glycosaminoglycans including heparin, hyaluronic acid, chondroitin sulfate and the like, and the like, as well as basal lamina (e.g., Bowman's membrane, Descemet's membrane, amniotic membrane and the like) comprised of these extracellular matrices.

An agent for promoting cell adhesion containing polypeptide of the present invention is intended for application to various clinical medicaments due to its cell adhesion promoting action as mentioned later. Moreover, its use as a research reagent is also provided by the present invention. An agent for promoting cell adhesion containing polypeptide of the present invention can be used as a reagent for researches for the study of extracellular matrix, study of cell signal transduction involving adhesion and the like.

It has been reported that cell adhesion to an extracellular matrix is important for cell survival (Frisch, S. M. et al., J. Cell Biol. 1994, 124, 619., Porcu, M., et al., Cornea 2007, 26, 73.). In the cornea, inhibition of cell adhesion due to the disappearance of laminin 5, which is one of the extracellular matrices, has also been reported to enhance death of corneal epithelial cells. Since the polypeptide of the present invention promotes adhesion of a corneal epithelial cell to the basal lamina (Bowman's membrane and the like) of corneal epithelium comprised of the extracellular matrix, it suppresses death of corneal epithelial cells on the surface layer of the eyes. Moreover, it is known that cell motilities consisting of division, migration (extension) and adhesion are involved in the repair of the corneal epithelium (Suzuki, K. et al., Prog. Retin. Eye Res. 2003, 22, 113). The polypeptide of the present invention promotes adhesion process in the cell motility, thereby promoting repair of corneal epithelial injury (i.e., wound or defect).

Therefore, a medicament containing the polypeptide of the present invention is useful for the treatment of a corneal epithelial disorder. As a specific disease causing a corneal epithelial disorder, keratitis due to physical or chemical stimulation, allergy, bacterial or fungal or virus infection and the like, corneal ulcer, corneal epithelial detachment (corneal erosion), corneal epithelial edema, corneal burn, cornea corrosion due to chemical substance and the like, dry eye, xerophthalmia, chronic superficial keratitis, superficial punctate keratopathy, corneal epithelial erosion, persistent corneal epithelial defects and the like can be mentioned, and is not particularly limited. The polypeptide of the present invention is particularly useful for the treatment of a corneal epithelial disorder associated with these diseases.

In addition, the polypeptide of the present invention has a promoting action of tear fluid secretion from lacrimal gland acinar cells. Tear fluid covers eyeball surface composing of cornea and conjunctiva, maintains wettability of the keratoconjunctiva, and prevents drying. In recent years, however, an increasing number of people complain about various symptoms such as tired feeling, feeling of foreign substance, i.e., dry eye syndrome, due to dried cornea-conjunctiva surface associated with tear fluid decreases, dry eye during wearing contact lenses, or dry eye during operation of office automation equipment and the like. Dry eye sometimes accompany corneal epithelial disorder, corneal epithelial erosion and the like due to disorder of corneal epithelial cells and, in serious cases, may develop corneal ulcer or ophthalmic infection. To alleviate such various symptoms associated with drying, an artificial tear fluid mainly containing salts such as sodium chloride and the like, and eye drops containing hydroxyethylcellulose, chondroitin sulfate or hyaluronic acid and the like are used. As the situation stands, however, a satisfactory agent has not been developed as yet. Although such symptomatic therapy can alleviate symptoms, it is not a causal therapy for a basic treatment. Tear fluid is considered to have, based on its inherent function, a therapeutic effect on keratoconjunctival disorders due to dry eye. Therefore, a substance that directly acts on the lacrimal gland to promote tear fluid secretion is expected to be a useful prophylactic or therapeutic drug for dry eye and diseases associated with dry eye.

While the dosage form of a pharmaceutical product containing the polypeptide of the present invention is not particularly limited, preferred are eye drops, eye washes, eye ointment, tablet and the like. More preferred is the form of an aqueous liquid (especially, eye drops) since it has significantly improved stability in aqueous solution. Here, the "aqueous liquid" means liquid with aqueous solvent. Examples of the aqueous solvent include, but are not limited to, distilled water for injection, purified water purified by ion-exchange resin or distillation, sterile purified water which is prepared by sterilizing the purified water, and the like. It is also preferable that the pharmaceutical product containing the polypeptide of the present invention is provided as a form of preparation to be dissolved when in use, which is reservable at room temperature after dissolution. These can be prepared by using a technique widely used. For example, eye drops can be prepared by appropriately blending additives such as isotonicity agent, buffering agent, pH adjuster, solubilizer, thickener, stabilizer, preservative and the like. In addition, stable eye drops can also be obtained by adding pH adjuster, thickener, dispersing agent and the like and suspending a drug.

Examples of the isotonicity agent include, but are not limited to, glycerol, propylene glycol, sodium chloride, potassium chloride, sorbitol, mannitol, glucose, boric acid and the like.

Examples of the buffering agent include, but are not limited to, phosphoric acid, phosphate, citric acid, acetic acid, ε-aminocaproic acid, trometamol, citrate, acetate, boric acid, glutamine, carbonate and the like.

Examples of the pH adjuster include, but are not limited to, hydrochloric acid, citric acid, phosphoric acid, acetic acid, sodium hydroxide, potassium hydroxide, boric acid, borax, sodium carbonate, sodium hydrogen carbonate and the like.

Examples of the solubilizer include, but are not limited to, polysorbate 80, polyoxyethylene hydrogenated castor oil 60, macrogol 4000 and the like.

Examples of the thickener and dispersing agent include, but are not limited to, cellulose polymers such as hydroxypropylmethylcellulose, hydroxypropylcellulose and the like, polyvinyl alcohol, polyvinylpyrrolidone and the like. Moreover, examples of the stabilizer include edetic acid, sodium edetate and the like.

Examples of the conventional preservative include, but are not limited to, sorbic acid, potassium sorbate, benzalkonium chloride, benzethonium chloride, methyl p-hydroxybenzoate, propyl p-hydroxybenzoate, chlorobutanol, boric acid, sodium edetate and the like. These preservatives may also be used in combination.

Eye drops containing the polypeptide of the present invention desirably has a pH of 4-8, and an osmotic pressure ratio of around 1.

In a pharmaceutical product containing the polypeptide of the present invention, the concentration of the polypeptide of the present invention can be set according to the symptom, age and the like and is not particularly limited. For example, when the polypeptide of the present invention is contained in eye drops, eye washes and the like, it is about 0.00003 w/v %-about 5 w/v %, preferably about 0.00001 w/v %-about 0.5 w/v %, about 0.0001 w/v %-about 0.0005 w/v %, about 0.001 w/v %-about 0.005 w/v %, about 0.01 w/v %-about 0.05 w/v %, more preferably about 0.003 w/v %-about 0.5 w/v %, most preferably about 0.001 w/v %-about 0.5 w/v %. The dose in the case of eye drops is, for example, one drop to several drops per ocular instillation, which is given once to several times per day. Eye drops may be a general ophthalmic solution, or an ophthalmic solution to be dissolved when in use.

A pharmaceutical product containing the polypeptide of the present invention as an active ingredient can be used for, for example, mammals (e.g., rat, mouse, guinea pig, bird, sheep, horse, bovine, swine, monkey, chimpanzee, human etc.) and the like.

EXAMPLES

The present invention is explained in detail in the following by referring to Examples, which are not to be construed as limitative.

Example 1

Synthesis of Polypeptide 1 (Pyr Lac50-83)

Polypeptide 1 was synthesized by a solid phase synthesis process. To be specific, a fluorenylmethoxycarbonyl (Fmoc) group was introduced into amino acid and the amino acid was supported by a resin. Then, an amide bond formation reaction was performed using dichloromethane as a solvent, and 2-(1H-benzotriazol-1-yl)-1,1,3,3-tetramethyluronium (HBTU) and N-methylpyrrolidone (NMP) as coupling reagents. The protecting group was eliminated by using DMF/20% piperidine. The obtained product was purified by high performance liquid chromatography (column: ODS, solvent: water/acetonitrile/0.05% TFA). As a result, polypeptide 1 of the following amino acid sequence was obtained.
Polypeptide 1: Pyr Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala (SEQ ID NO: 1)
wherein "Pyr" means pyroglutamic acid.
Bachem (manufacturer and supplier): Product No. 4064390
white powder MALDI-TOF-MS Calcd.: 3636.20. Found: 3636.89.
Purity (HPLC A/A %)>92%

Comparative Example 1

Synthesis of Polypeptide 2 (Lac50-83)

In the same manner as in Example 1, polypeptide 2 of the following amino acid sequence was obtained.
polypeptide 2: Gln Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala (SEQ ID NO: 2)
Biosynthesis Inc. (manufacturer)
white powder MALDI-TOF-MS Calcd.: 3653.27. Found: 3652.28.
Purity (HPLC A/A %) 99.26%

Comparative Example 2

Synthesis of Polypeptide 3 (Pyr Lac50-94)

In the same manner as in Example 1, polypeptide 3 of the following amino acid sequence was obtained.
polypeptide 3: Pyr Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala Gly Lys Gly Met His Gly Gly Val Pro Gly Gly (SEQ ID NO: 3)
wherein "Pyr" means pyroglutamic acid.
Bachem (manufacturer and supplier): Product No. 4064388
white powder MALDI-TOF-MS Calcd.: 4571.28. Found: 4571.40.
Purity (HPLC A/A %): >90%

Comparative Example 3

Synthesis of Polypeptide 4 (Lac50-94)

In the same manner as in Example 1, polypeptide 4 of the following amino acid sequence was obtained.
polypeptide 4: Gln Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala Gly Lys Gly Met His Gly Gly Val Pro Gly Gly (SEQ ID NO: 4)
Biosynthesis Inc. (manufacturer)
white powder MALDI-TOF-MS Calcd.: 4588.35. Found: 4590.14.
Purity (HPLC A/A %) 96.88%

Comparative Example 4

Synthesis of Polypeptide 5 (Lac49-83)

In the same manner as in Example 1, polypeptide 5 of the following amino acid sequence was obtained.
polypeptide 5: Val Gln Gly Thr Ala Lys Val Thr Ser Ser Arg Gln Glu Leu Asn Pro Leu Lys Ser Ile Val Glu Lys Ser Ile Leu Leu Thr Glu Gln Ala Leu Ala Lys Ala (SEQ ID NO: 9)
Biosynthesis Inc. (manufacturer)
white powder MALDI-TOF-MS Calcd.: 3752.4. Found: 3751.38.
Purity (HPLC A/A %) 96.13%

Experimental Example 1

Influence of Pyro-Modification on Stability of Partial Peptide of Lacritin in Aqueous Solution When the partial peptide of lacritin of the present invention is produced as a medicament, particularly, a medicament provided in the form of an aqueous liquid, stability thereof in aqueous solution is desired. Therefore, an influence of pyro-modification of N-terminal glutamine in the present invention on the stability in aqueous solution was examined.

Using Pyr Lac50-83 produced in Example 1 and Lac50-83 produced in Comparative Example 1, and changing preservation conditions in PBS (Phosphate-Buffered Salines, pH 7.2 (Invitrogen); component (/100 mL): $KH_2PO_4$ 0.021 g, $NaH_2PO_4$ 0.0726 g, NaCl 0.9 g) variously, the residual ratio (%) of the peptide content was measured. The concentration of each peptide was $10^{-4}$ M. Pyr Lac50-83 and Lac50-83 are polypeptides solely different in the presence of pyro-modification (Pyr Lac50-83) or absence of pyro-modification (Lac50-83), of N-terminal glutamine, as is clear from the above-mentioned amino acid sequence.

[Preservation Conditions]
temperature: 4° C., 25° C., 40° C., 60° C.
period: 7 days, 14 days, 21 days, 28 days Both polypeptides were preserved under respective preservation conditions, peptide content was measured by HPLC chromatography, and the residual ratio thereof was calculated. In addition, the residual ratio was calculated by the following formula 1, while taking into consideration as far as possible water evaporation from the preservation container.

residual rate (after water correction) (%)=residual rate (%) before water correction×(100−water permeation rate (%) of container)/100    [formula 1]

wherein "the water permeation rate of container" is obtained by measuring the weight of empty container (tare weight), and sample weight before and after preservation, and calculating according to the following formula 2.
(wherein the sample weight is the total weight of preservation container and solution)

water permeation rate (%) of container=(sample weight (g) before preservation−sample weight (g) after preservation under each condition)/(sample weight (g) before preservation−weight (g) of empty preservation container)×100    [formula 2]

[HPLC Chromatography Conditions]
detector: ultraviolet absorption spectrophotometer (measurement wavelength: 220 nm)
column: commercially available column of a stainless tube with inner diameter 4.6 mm, length 150 mm, which is filled with liquid chromatography octadecylsilylated silica gel with average particle size of 5 μm was used.
(Capcel pak C18 UG120 Å, S5 μm 4.6 mm×150 mm, Shiseido Co., Ltd.)
column temperature: constant temperature near 20° C.
mobile phase A: trifluoroacetic acid solution (0.5→1000) (solvent: purified water)
mobile phase B: trifluoroacetic acid solution (0.5→1000) (solvent: acetonitrile)
solution sending of mobile phase: the mixing ratio of mobile phase A and mobile phase B was changed as follows to control linear density gradient.

| time (min) after injection | mobile phase A (vol %) | mobile phase B (vol %) |
|---|---|---|
| 0-2.5 | 90 | 10 |
| 2.5-27.5 | 90→35 | 10→65 |
| 27.5-30 | 35→10 | 65→90 |
| 30-35 | 10 | 90 |
| 35-40 | 10→90 | 90→10 |
| 40-50 | 90 | 10 | flow: 0.5 mL/min
Autosampler temperature: constant temperature near 4° C.
Injector washing: acetonitrile aqueous solution (50→100) (solvent: purified water)

The results are shown in FIG. 1.

It was found that pyro-modification enables longer-term preservation in aqueous solution, and preservation at a higher temperature.

Experimental Example 2

Promoting Effect by Partial Peptide of Lacritin on Adhesion of Human Corneal Epithelial Cell to Extracellular Matrix In Experimental Example 1, pyro-modification of N-terminal glutamine was found to markedly improve stability of polypeptide in aqueous solution. Thus, whether or not the inherent property of partial peptide of lacritin, i.e., cell adhesion promoting effect, is influenced by pyro-modification was examined.

As a negative control, lacritin peptides (Lac24-56, Lac50-65) having different sequence from that of the present invention were used. These peptides were prepared in the same manner as in the aforementioned peptide.
polypeptide Lac24-56
Glu Ile Ser Gly Pro Ala Glu Pro Ala Ser Pro Pro Glu Thr Thr Thr Thr Ala Gln Glu Thr Ser Ala Ala Ala Val Gln Gly Thr Ala Lys Val Thr (SEQ ID NO: 7)
Bachem (manufacturer and supplier): Product No. 4064384
polypeptide Lac50-65
Gln Gly Thr Ala Lys Val Thr Ser Ser Arg Gln Glu Leu Asn Pro Leu (SEQ ID NO: 8)
Biosynthesis Inc. (manufacturer)

An extracellular matrix solution (10 μg/mL, collagen type IV: Becton, Dickinson and Company, catalog No. 354245) was added to a 96 well plate (Iwaki Glass Company, Limited, catalog No. 3860-096). The solution was incubated at 37° C. for 1 hr to coat the plate with the extracellular matrix. After the redundant extracellular matrix solution was removed, 0.1% BSA solution (Sigma-Aldrich Co., catalog No. A3803) was added to block the region not coated with the extracellular matrix. Successively, the BSA solution was removed and the plate was washed twice with PBS, and polypeptides 1-4 (concentration 100 μg/mL) synthesized in Example 1 (Pyr Lac50-83) and Comparative Examples 1-3 (Lac50-83, Pyr Lac50-94, Lac50-94), and negative control polypeptide (Lac24-56, Lac50-65) were added by 50 μl, per well. Furthermore, established human corneal epithelial cells (HCE-T: can be prepared by the method described in Invest Ophthalmol Vis Sci. 1995, 36, 614) were cultured overnight under serum-free conditions and added to the plate at 2×10⁴ cells/100 μL DMEM/F12 medium/well. The plate was incubated at 37° C. for 25 min to allow adhesion of the cells to the plate.

Thereafter, the cells were fixed with 10% neutral buffered formaldehyde liquid (NACALAI TESQUE, INC., catalog No. 37152-51), and stained with 1% crystal violet staining solution (Sigma-Aldrich Co., catalog No. C3886). The image of the stained cells was uploaded using an inverted system microscope (Olympus Corporation, IX71), and the area of the adhered cells was measured using Image-Pro Plus Ver. 4.5 (Nippon Roper K.K.). The cell adhesion rate obtained based on that without addition of polypeptide as 100% is shown in FIG. 2.

As is clear from FIG. 2, polypeptide 1 (Pyr Lac50-83) was confirmed to have an activity to promote cell adhesion between a corneal epithelial cell and extracellular matrix, and confirmed to be free of influence of pyro-modification of N-terminal glutamine in Lac50-83. On the other hand, polypeptide 3 (Pyr Lac50-94) showed lowered activity as compared to that of polypeptide before pyro-modification (polypeptide 4: Lac50-94), and pyro-modification of N-terminal glutamine of Lac50-94 was found to attenuate a cell adhesion promoting effect.

From the above results, it was confirmed that the lacritin partial polypeptide of the present invention is superior in that it improves stability in aqueous solution while maintaining a cell adhesion promoting effect.

Experimental Example 3

Promoting Effect by Partial Peptide of Lacritin on Secretion of Tear Fluid Protein from Monkey Lacrimal Gland Acinar Cells (Preparation of Acinar Cells)

The lacrimal glands of three monkeys (*Macaca fascicularis*) were obtained from eve bio-science and used for the experiment. The detail of the three monkeys used is as follows.

9 years 6 months (male, Vietnam)
10 years 9 months (male, China)
10 years 8 months (male, Vietnam)

The lacrimal gland thereof was minced in DMEM/F12 (Invitrogen Corporation, catalog No. 11330) containing 0.1 mg/mL Trypsin inhibitor (Sigma, catalog No. T9003). Then, HBSS (Invitrogen Corporation, catalog No. 14175) containing 0.76 mg/mL EDTA (Wako Pure Chemical Industries, Ltd., catalog No. 345-01865) was added to the lacrimal gland and the mixture was gently shaken at 37° C. for 7-12 min. Thereafter, the supernatant was removed by centrifugation, DMEM/F12 medium containing 200 U/mL collagenase A (Roche, catalog No. 11088785103), 698 U/mL Hyarulonidase (Worthington, catalog No. LS002592), 10 U/mL DNase (Roche, catalog No. 4536282) (CHD) was added, and the mixture was gently shaken at 37° C. for 10-40 min. The above-mentioned step was performed twice. Thereafter, 20% FBS (Invitrogen Corporation, catalog No. 10082-147) was added to quench the enzyme reaction, and the cells were dispersed by a pipetting operation. The residue was removed with 100 μm (Becton, Dickinson and Company, catalog No. 352360) and 40 μm (Becton, Dickinson and Company, catalog No. 352340) cell strainers. The cells were separated by 10%, 30%, 60% Percoll (Sigma, catalog No. P4937) and the cells that gathered between 30% and 60% were taken as acinar cells.

(Detection of Tear Fluid Protein Lactoferrin Secreted in Medium)

The monkey acinar cells prepared in this Experimental Example were plated in a plate coated with rat collagen, Type I (0.01 mg/cm$^2$; BD Biosciences, catalog No. 354236), and cultured in DMEM/F12 medium containing 10 ng/ml dexamethasone (Sigma, catalog No. D2915), 1 mM putrescine (Sigma, catalog No. P5780), 50 ng/ml EGF (Invitrogen Corporation, PHG0311), 25 μg/ml L-ascorbic acid (Sigma, catalog No. A4544), 1× Insulin-transferrin-sodium selenite media supplement (Sigma, catalog No. 11884), 10 μg/mL Glutathione (Sigma, catalog No. G6013) and 50 μg/ml gentamicin (Invitrogen Corporation, catalog No. 15750) for 1 day. The next day, preincubation was performed for 30 min in DMEM/F12 medium free of supplement. Then, DMEM/F12 containing partial peptide of lacritin was added, and the mixture was incubated at 37° C. for 10 min and the medium was recovered.

As lacritin polypeptide, polypeptide 1 (Pyr Lac50-83) and polypeptide 2 (Lac50-83) were used. As the control group, PBS was used instead of polypeptide.

The collected medium was purified by ReadyPrep 2D clean up kit (Bio-Rad Laboratories, Inc., catalog No. 163-2130), dissolved in NuPAGE LDS sample buffer (Invitrogen Corporation, catalog No. NP0007), and thermally denatured at 70° C. for 10 min. An equivalent amount of a sample was electrophoresed in 4-12% NuPAGE Novex Bis Tris gel (Invitrogen Corporation, catalog No. NP0322BOX) in MES buffer (Invitrogen Corporation, catalog No. NP0002) at 200 V for 35 min, and blotted on a PVDF membrane (Nihon Millipore K.K., catalog No. IPVH00010) at 100 V for 60 min using Trans Blot Mini Cell (Bio-Rad Laboratories, Inc.). The membrane was blocked with TTBS (Bio-Rad Laboratories, Inc., catalog No. 170-6435) containing 0.5% skim-milk (Wako Pure Chemical Industries, catalog No. 198-10605) at room temperature for 30 min, and reacted overnight at 4° C. with lactoferrin antibody (Sigma-Aldrich Co., catalog No. L-3263) diluted 10000-fold. After washing the membrane with TTBS, the membrane was reacted at room temperature for 60 min with anti-rabbit HRP secondary antibody, which was diluted 10000-fold. Then band(s) were detected and measured using ECL plus (GE healthcare, catalog No. RPN2132).

Figure 3:
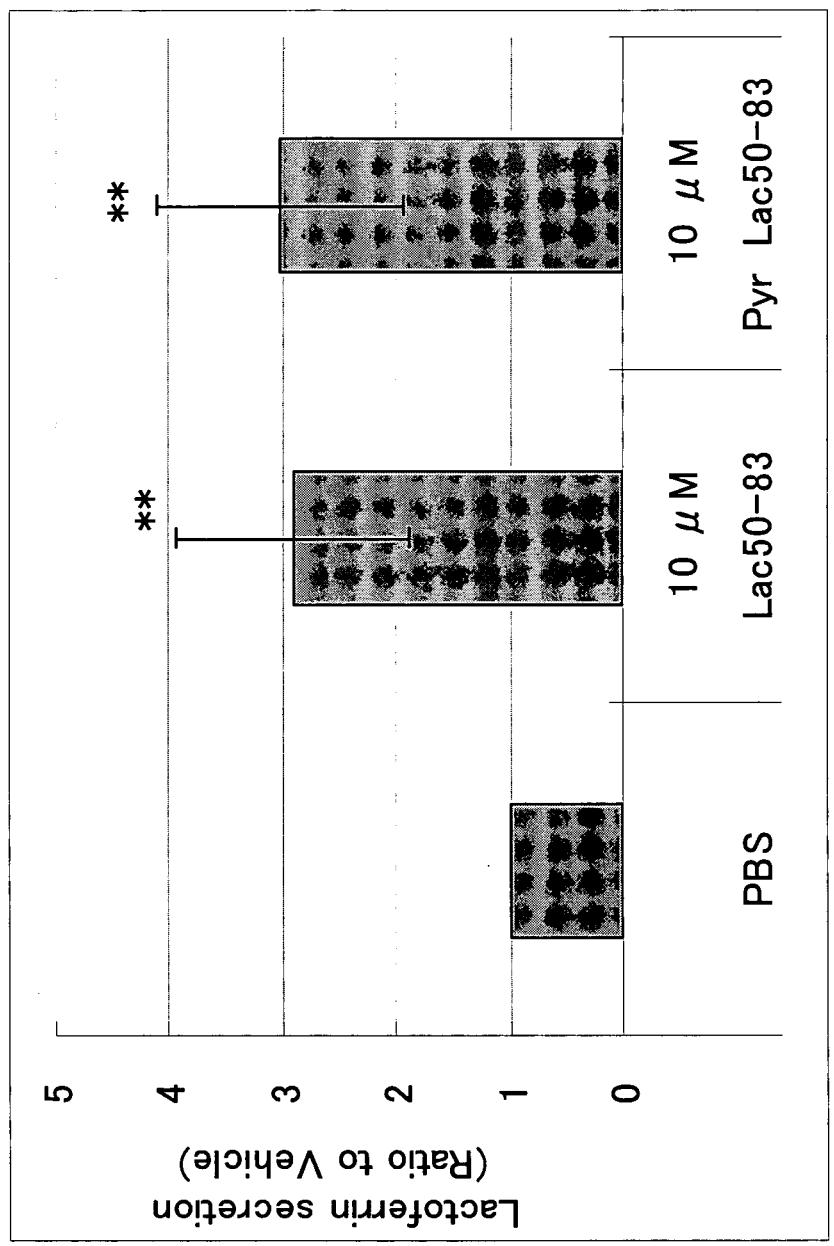
FIG. 3 is a graph showing the results of the promoting effect of partial peptides of lacritin on tear protein (lactoferrin) secretion from monkey lacrimal gland acinar cells, wherein the vertical axis shows the amount of lactoferrin secreted in the medium against PBS as 100%, and the horizontal axis shows evaluated various peptides.

The results are shown in FIG. 3. Three monkeys were used in this Experimental Example, one sample was taken from each of the first and second monkeys and two samples were taken from the third monkey, 4 samples in total.

Experimental Example 4

Promoting Effect by Partial Peptide of Lacritin on Secretion of Tear Fluid Protein from Rat and Rabbit Lacrimal Gland Acinar Cells (Preparation of Acinar Cells)

The lacrimal gland of rat and rabbit is minced in DMEM/F12 (Invitrogen Corporation, catalog No. 11330) containing 0.1 mg/mL Trypsin inhibitor (Sigma, catalog No. T9003). Then, HBSS (Invitrogen Corporation, catalog No. 14175) containing 0.76 mg/mL EDTA (Wako Pure Chemical Industries, Ltd., catalog No. 345-01865) is added and the mixture is gently shaken at 37° C. for 15-20 min. Thereafter, the supernatant is removed by centrifugation, DMEM/F12 medium containing 200 U/mL collagenase A (Roche, catalog No. 11088785103), 698 U/mL Hyarulonidase (Worthington, catalog No. LS002592), 10 U/mL DNase (Roche, catalog No. 4536282) (CHD) is added, and the mixture is gently shaken at 37° C. for 15-50 min. The above-mentioned step is performed twice. Thereafter, 20% FBS (Invitrogen Corporation, catalog No. 10082-147) is added to quench the enzyme reaction, and the cells are dispersed by a pipetting operation. The residue is removed with 100 μm (Becton, Dickinson and Company, catalog No. 352360) and 40 μm (Becton, Dickinson and Company, catalog No. 352340) cell strainers. The cells are separated by 10%, 30%, 60% Percoll (Sigma, catalog No. P4937) and the cells that gathered between 30% and 60% are taken as acinar cells.

(Detection of Tear Fluid Protein Lactoferrin Secreted in Medium)

The acinar cells of rat and rabbit are plated in a plate coated with rat collagen, Type I (0.01 mg/cm$^2$; BD Biosciences, catalog No. 354236), and cultured in DMEM/F12 medium containing 10 ng/ml dexamethasone (Sigma, catalog No. D2915), 1 mM putrescine (Sigma, catalog No. P5780), 50 ng/ml EGF (Invitrogen Corporation, PHG0311), 25 µg/ml L-ascorbic acid (Sigma, catalog No. A4544), 1× Insulin-transferrin-sodium selenite media supplement (Sigma, catalog No. 11884), 10 µg/mL Glutathione (Sigma, catalog No. G6013) and 25 µg/ml gentamicin (Invitrogen Corporation, catalog No. 15750) for 1 day in a $CO_2$ incubator. The next day, preincubation is performed for 30 min in DMEM/F12 medium free of supplement. Then, DMEM/F12 containing partial peptide of lacritin is added, and the mixture is incubated at 37° C. for 30 min or 60 min and the medium is recovered.

As the amount of the tear fluid protein secreted in the medium, peroxidase activity can be measured using Amplex Red Hydrogen Peroxide/Peroxidase Assay Kit (Invitrogen Corporation, catalog No. A22188), albumin amount can be measured using Rat Albumin ELISA Quantitation Set (Bethyl Laboratories Inc., catalog No. E100-125-12), and IgA amount can be measured using Rat IgA ELISA Quantitation Set (Bethyl Laboratories Inc., catalog No. E100-102).

Experimental Example 5

Promoting Effect by Partial Peptide of Lacritin on Secretion of Tear Fluid Protein from Monkey Lacrimal Gland Acinar Cells in the Presence of Cytokine Cytokine has an action to decrease secretion of tear fluid protein from acinar cells. In this Example, the presence or absence of an effect to promote secretion of tear fluid protein by partial peptide of lacritin in acinar cells showing decreased tear fluid secretion function due to cytokine can be examined.

The lacrimal gland of monkey is minced in DMEM/F12 (Invitrogen Corporation, catalog No. 11330) containing 0.1 mg/mL Trypsin inhibitor (Sigma, catalog No. T9003). Then, HBSS (Invitrogen Corporation, catalog No. 14175) containing 0.76 mg/mL EDTA (Sigma, catalog No. E-5134) is added and the mixture is gently shaken at 37° C. for 7-20 min. Thereafter, the supernatant is removed by centrifugation, DMEM/F12 medium containing 200 U/mL collagenase A (Roche, catalog No. 11088785103), 698 U/mL Hyaluronidase (Worthington, catalog No. LS002592) and 10 U/mL DNase (Roche, catalog No. 4536282) (CHD) is added, and the mixture is gently shaken in an incubator at 37° C. for 15-50 min. The above-mentioned step is performed twice. Thereafter, 20% FBS (Invitrogen Corporation, catalog No. 10082-147) is added to quench the enzyme reaction, and the cells are dispersed by a pipetting operation. The residue is removed with 100 µm (Becton, Dickinson and Company, catalog No. 352360) and 40 µm (Becton, Dickinson and Company, catalog No. 352340) cell strainers. The cells are separated by 10%, 30%, 60% Percoll (Sigma, catalog No. P4937) and the cells that gathered between 30% and 60% are taken as acinar cells.

The acinar cells of monkey are plated in a plate coated with rat collagen, Type I (0.01 mg/cm$^2$; BD Biosciences, catalog No. 354236), and cultured in DMEM/F12 medium (cell culture medium) containing 10 ng/ml dexamethasone (Sigma, catalog No. D2915), 1 mM putrescine (Sigma, catalog No. P5780), 50 ng/ml EGF (Invitrogen Corporation, PHG0311), 50 µg/ml L-ascorbic acid (Sigma, catalog No. A4544), 1× Insulin-transferrin-sodium selenite media supplement (Sigma, catalog No. 11884), 10 µg/mL Glutathione (Sigma, catalog No. G6013) and 25 µg/ml gentamicin (Invitrogen Corporation, catalog No. 15750) for 1 day in a $CO_2$ incubator. The next day, the medium was changed to a cell culture medium containing 10 ng/mL TNF-alpha (R&D Systems, catalog No. 210-TA) and 10 ng/mL of IFN-gamma (R&D Systems, catalog No. 285-IF), and the cells are cultivated in a $CO_2$ incubator for one more day. Thereafter, DMEM/F12 containing partial peptide of lacritin is added and, after stimulation for 10 min in a $CO_2$ incubator, the medium is recovered. The recovered medium is desalted and concentrated by ReadyPrep 2D Cleanup Kit (Bio-Rad Laboratories, Inc., catalog No. 163-2130), dissolved in NuPAGE LDS sample buffer (Invitrogen, catalog No. NP0007), and denatured by heating at 70° C. for 10 min. An equivalent amount of a sample is separated in 4-12% NuPAGE Bis-Tris gel, MES buffer at 200 V for 35 min at room temperature, and blotted on PVDF membrane using Transblot Mini Cell (Bio-Rad Laboratories, Inc.) at 100 V for 60 min. The membrane is subjected to blocking using TTBS containing 0.5% skim milk at room temperature for 30 min and reacted with 5000-fold diluted lactoferrin antibody (Sigma, catalog No. L3262) overnight at 4° C. After washing with TTBS, anti-rabbit HRP secondary antibody (Santa Cruz Biotechnology, Inc., catalog No. sc-2054) is diluted 10000-fold and reacted at room temperature for 60 min. Then, lactoferrin is detected using ECL plus (GE Healthcare, catalog No. RPN2132).

Experimental Example 6

Anterior Ocular Segment Stimulation Test

In this Experimental Example, an eye drop containing each polypeptide was instilled and irritation in the anterior ocular segment was evaluated.

Polypeptide 1 (Pyr Lac50-83) ophthalmic solution and polypeptide 5 (Lac49-83) ophthalmic solution were prepared by diluting each polypeptide with PBS [obtained by dissolving sodium chloride 0.9 g (NACALAI TESQUE, INC., catalog No. 31320-05) and sodium dihydrogen phosphate 0.1 g (NACALAI TESQUE, INC., catalog No. 31718-15) with distilled water to the total amount of 100 ml (pH 7.0)] to 1 mM concentration.

Polypeptide 1 ophthalmic solution, polypeptide 5 ophthalmic solution or PBS (control group) was instilled 8 times to male Japanese white rabbit (KITAYAMA LABES Co., Ltd., body weight about 2.0 kg; N=1 in polypeptide 1 administration group and N=2 in polypeptide 5 administration group) by 100 µL one time, 1 hr interval. The observations of anterior ocular segment and the observation of corneal staining plaque with fluorescein (Wako Pure Chemical Industries, Ltd., catalog No. 213-00092) were performed before ocular instillation and 30 min after final ocular instillation. Irritant property in the anterior ocular segment was evaluated by McDonald-Shadduck method (Hackett, R. B. and McDonald, T. O., Chapter 44: Assessing Ocular Irritation, Dermatotoxicology fifth edition, Francis N. Marzulli and Howard I. Maibach, Taylor & Francis, U.S.A.: 557-567, 1996).

The anterior ocular segment after ocular instillation was observed for cornea, iris, and conjunctiva. As a result, as to the cornea, transparency was normal; cloudiness and vascularization in the corneal stroma were not found; and corneal staining plaque due to fluorescein was not observed. As to the iris, optical response was normal; and iris congestion was not found. As to the conjunctiva, conjunctival congestion and swelling were not found, and the conjunctiva was normal. In addition, abnormal secreted material was not observed. These results correspond to score 0 according to the evaluation by McDonald-Shadduck method (see below), and abnormality was not observed with both polypeptide 1 ophthalmic solution and polypeptide 5 ophthalmic solution. Moreover, both ophthalmic solutions showed no abnormality in the observation of corneal staining plaque. Therefrom it has been clarified that polypeptide 1 ophthalmic solution and polypeptide 5 ophthalmic solution have high safety.

Criteria For Determining Score 0

A) Conjunctival congestion; normal, without congestion. Blood vessels are sometimes observed in the perilimbal region and the palpebral and bulbar conjunctiva around 12:00 and 6:00 o'clock positions.
B) Conjunctival swelling; normal, without swelling.
C) Secreted material; normal, without secretion.
D) Optical response of iris; normal pupil response.
E) Iris congestion; normal. A congested area of about 1 mm to 2 mm in diameter is sometimes observed near the pupillary border around the 12:00 to 1:00 o'clock position and 6:00 to 7:00 o'clock position.
F) Transparency of cornea; normal.
G) Level of corneal cloudiness; normal cornea without cloudiness.
H) Vascularization in corneal stroma; no vascularization.
J) Staining of cornea by fluorescein staining; no fluorescein staining.

Formulation Example 1

Culture Medium for Preparation of Corneal Epithelial Sheet

Four milliliters of HCGS growth additive (contents: mEGF, hydrocortisone, insulin, transferrin and BPE, KURABO INDUSTRIES LTD. catalogue No. KC-6150) and 15 mg of polypeptide 1 are added to EpiLife medium (corneal epithelial cell basal medium, Cascade Biologics, catalogue No. M-EPI-500-CA) to give a culture medium (total amount 500 mL).

Formulation Example 2

Eye Drop Containing Lacritin Partial Peptide

The eye drop shown below is prepared according to a conventional method.

| | |
|---|---|
| polypeptide 1 | 0.5 g |
| sodium dihydrogen phosphate | 0.1 g |
| sodium chloride | 0.9 g |
| sodium hydroxide | e.q. |
| sterilized purified water | e.q. |
| total amount | 100 mL (pH 7) |

INDUSTRIAL APPLICABILITY

According to the present invention, a novel polypeptide that promotes adhesion between a cell and extracellular matrix, particularly adhesion between a corneal epithelial cell and extracellular matrix, and is stable in aqueous solution can be provided. Since the polypeptide of the present invention can promote adhesion between a corneal epithelial cell and extracellular matrix, and is stable in aqueous solution, a medicament superior in preservation stability, particularly such medicament in the form of an aqueous liquid, can be provided.

DESCRIPTION OF SEQUENCE LISTING

SEQ ID NO: 1 amino acid sequence of pyro-modified partial peptide of lacritin (Pyr Lac50-83)
SEQ ID NO: 2 amino acid sequence of partial peptide of lacritin (Lac50-83)
SEQ ID NO: 3 amino acid sequence of pyro-modified partial peptide of lacritin (Pyr Lac50-94)
SEQ ID NO: 4 amino acid sequence of peptide of lacritin (Lac50-94)
SEQ ID NO: 5 amino acid sequence of full-length lacritin (human)
SEQ ID NO: 6 amino acid sequence of acetylated partial peptide of lacritin
SEQ ID NO: 7 amino acid sequence of partial peptide of lacritin (Lac24-56)
SEQ ID NO: 8 amino acid sequence of partial peptide of lacritin (Lac50-65)
SEQ ID NO: 9 amino acid sequence of partial peptide of lacritin (Lac49-83)

SEQUENCE LISTING FREE TEXT

SEQ ID NO: 1: Xaa shows pyroglutamic acid.
SEQ ID NO: 3: Xaa shows pyroglutamic acid.
This application is based on a patent application No. 2009-215030 filed in Japan, the contents of which are incorporated in full herein.

The invention claimed is:

1. An isolated polypeptide comprising the amino acid sequence of SEQ ID NO: 1.

2. A method of promoting corneal epithelial cell adhesion, comprising contacting a corneal epithelial cell with an effective concentration of the polypeptide of claim 1.

3. A medicament comprising the polypeptide of claim 1 as an effective ingredient.

4. The medicament of claim 3, which is aqueous liquid.

5. A method for the treatment of a corneal epithelium disorder in a patient in need thereof, which comprises administering an effective amount of the polypeptide of claim 1, wherein the corneal epithelium disorder is dry eye or a disease associated with dry eye.

* * * * *

SEQUENCE LISTING

<160> NUMBER OF SEQ ID NOS: 9

<210> SEQ ID NO 1
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa is a pyroglutamate.

<400> SEQUENCE: 1

Xaa Gly Thr Ala Lys Val Thr Ser Ser Arg Gln Glu Leu Asn Pro Leu

-continued

```
                  1               5                  10                  15
Lys Ser Ile Val Glu Lys Ser Ile Leu Leu Thr Glu Gln Ala Leu Ala
                 20                  25                  30

Lys Ala

<210> SEQ ID NO 2
<211> LENGTH: 34
<212> TYPE: PRT
<213> ORGANISM: Homo sapiens

<400> SEQUENCE: 2

Gln Gly Thr Ala Lys Val Thr Ser Ser Arg Gln Glu Leu Asn Pro Leu
1               5                  10                  15

Lys Ser Ile Val Glu Lys Ser Ile Leu Leu Thr Glu Gln Ala Leu Ala
                 20                  25                  30

Lys Ala

<210> SEQ ID NO 3
<211> LENGTH: 45
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa is a pyroglutamate.

<400> SEQUENCE: 3

Xaa Gly Thr Ala Lys Val Thr Ser Ser Arg Gln Glu Leu Asn Pro Leu
1               5                  10                  15

Lys Ser Ile Val Glu Lys Ser Ile Leu Leu Thr Glu Gln Ala Leu Ala
                 20                  25                  30

Lys Ala Gly Lys Gly Met His Gly Gly Val Pro Gly Gly
                 35                  40                  45

<210> SEQ ID NO 4
<211> LENGTH: 45
<212> TYPE: PRT
<213> ORGANISM: Homo sapiens

<400> SEQUENCE: 4

Gln Gly Thr Ala Lys Val Thr Ser Ser Arg Gln Glu Leu Asn Pro Leu
1               5                  10                  15

Lys Ser Ile Val Glu Lys Ser Ile Leu Leu Thr Glu Gln Ala Leu Ala
                 20                  25                  30

Lys Ala Gly Lys Gly Met His Gly Gly Val Pro Gly Gly
                 35                  40                  45

<210> SEQ ID NO 5
<211> LENGTH: 138
<212> TYPE: PRT
<213> ORGANISM: Homo sapiens

<400> SEQUENCE: 5

Met Lys Phe Thr Thr Leu Leu Phe Leu Ala Ala Val Ala Gly Ala Leu
1               5                  10                  15

Val Tyr Ala Glu Asp Ala Ser Asp Ser Thr Gly Ala Asp Pro Ala
                 20                  25                  30

Gln Glu Ala Gly Thr Ser Lys Pro Asn Glu Glu Ile Ser Gly Pro Ala
                 35                  40                  45

Glu Pro Ala Ser Pro Pro Glu Thr Thr Thr Ala Gln Glu Thr Ser
                 50                  55                  60
```

Ala Ala Ala Val Gln Gly Thr Ala Lys Val Thr Ser Ser Arg Gln Glu
65                  70                  75                  80

Leu Asn Pro Leu Lys Ser Ile Val Glu Lys Ser Ile Leu Leu Thr Glu
                85                  90                  95

Gln Ala Leu Ala Lys Ala Gly Lys Gly Met His Gly Val Pro Gly
            100                 105                 110

Gly Lys Gln Phe Ile Glu Asn Gly Ser Glu Phe Ala Gln Lys Leu Leu
        115                 120                 125

Lys Lys Phe Ser Leu Leu Lys Pro Trp Ala
        130                 135

<210> SEQ ID NO 6
<211> LENGTH: 34
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 6

Gln Gly Thr Ala Lys Val Thr Ser Ser Arg Gln Glu Leu Asn Pro Leu
1               5                   10                  15

Lys Ser Ile Val Glu Lys Ser Ile Leu Leu Thr Glu Gln Ala Leu Ala
            20                  25                  30

Lys Ala

<210> SEQ ID NO 7
<211> LENGTH: 33
<212> TYPE: PRT
<213> ORGANISM: Homo sapiens

<400> SEQUENCE: 7

Glu Ile Ser Gly Pro Ala Glu Pro Ala Ser Pro Pro Glu Thr Thr Thr
1               5                   10                  15

Thr Ala Gln Glu Thr Ser Ala Ala Val Gln Gly Thr Ala Lys Val
            20                  25                  30

Thr

<210> SEQ ID NO 8
<211> LENGTH: 16
<212> TYPE: PRT
<213> ORGANISM: Homo sapiens

<400> SEQUENCE: 8

Gln Gly Thr Ala Lys Val Thr Ser Ser Arg Gln Glu Leu Asn Pro Leu
1               5                   10                  15

<210> SEQ ID NO 9
<211> LENGTH: 35
<212> TYPE: PRT
<213> ORGANISM: Homo sapiens

<400> SEQUENCE: 9

Val Gln Gly Thr Ala Lys Val Thr Ser Ser Arg Gln Glu Leu Asn Pro
1               5                   10                  15

Leu Lys Ser Ile Val Glu Lys Ser Ile Leu Leu Thr Glu Gln Ala Leu
            20                  25                  30

Ala Lys Ala
35